(12) United States Patent
Al Nabulsi et al.

(10) Patent No.: US 11,260,142 B2
(45) Date of Patent: Mar. 1, 2022

(54) DISPOSABLE CONTAINER

(71) Applicants: Abdulilah Mohammed M. Al Nabulsi, Sakaka (SA); Abdulaziz Mohammed M. Alnabulsi, Sakaka (SA)

(72) Inventors: Abdulilah Mohammed M. Al Nabulsi, Sakaka (SA); Abdulaziz Mohammed M. Alnabulsi, Sakaka (SA)

(*) Notice: Subject to any disclaimer, the term of this patent is extended or adjusted under 35 U.S.C. 154(b) by 0 days.

(21) Appl. No.: 17/051,159

(22) PCT Filed: Jan. 24, 2020

(86) PCT No.: PCT/IB2020/050559
§ 371 (c)(1),
(2) Date: Oct. 27, 2020

(87) PCT Pub. No.: WO2020/174294
PCT Pub. Date: Sep. 3, 2020

(65) Prior Publication Data
US 2021/0187146 A1 Jun. 24, 2021

(30) Foreign Application Priority Data
Feb. 27, 2019 (SG) .............................. 10201901774T (51) Int. Cl.
*A61L 9/12* (2006.01)
*A45D 20/12* (2006.01)
(Continued)

(52) U.S. Cl.
CPC .............. *A61L 9/12* (2013.01); *A45D 20/122* (2013.01); *A61L 9/014* (2013.01); *A61L 9/03* (2013.01);
(Continued)

(58) Field of Classification Search
CPC ... A61L 9/12; A61L 9/014; A61L 9/03; A61L 9/048; A61L 2209/133; A61L 2209/14;
(Continued)

(56) References Cited

U.S. PATENT DOCUMENTS 3,902,877 A 9/1975 Swaim
4,835,879 A * 6/1989 Egelstad ................ A45D 20/12
34/72

(Continued)

FOREIGN PATENT DOCUMENTS

JP H07-12004 U 2/1995
JP H09201407 8/1997
(Continued)

OTHER PUBLICATIONS

Hosokawa full translation (Year: 2006).*
Woo full translation (Year: 2000).*

*Primary Examiner* — Sean E Conley
*Assistant Examiner* — Brendan A Hensel
(74) *Attorney, Agent, or Firm* — Maschoff Brennan (57) ABSTRACT

The present invention relates to a disposable container (100). The disposable container (100) is use particularly for vaporization, evaporation or diffusion whereby filler materials of filler means are released into the air flow stream through air flow means. The disposable container (100) comprising filler means (101) filled with filler materials within the closed empty space between an inner side wall (101a) and an outer side wall (101b) and a top (101c) and a bottom part (101d) of the disposable container (100); and locking means (104) at the bottom part of the disposable container (100) to further secure the disposable container (100) to an air flow means. The inner side wall (101a), the outer side wall (101b), the top (101c) and the bottom part (101d) of the disposable container (100) are permeable or perforated enabling filler materials to be released into an air (Continued)

flow stream through air flow means; wherein filler materials are released by means of vaporization, evaporation or diffusion.

8 Claims, 7 Drawing Sheets

(51) Int. Cl.
    *A61L 9/014*     (2006.01)
    *A61L 9/03*     (2006.01)
    *A61L 9/04*     (2006.01)
    *D06F 58/20*     (2006.01)

(52) U.S. Cl.
    CPC ............ *A61L 9/048* (2013.01); *D06F 58/203* (2013.01); *A61L 2209/133* (2013.01); *A61L 2209/14* (2013.01); *A61L 2209/15* (2013.01); *A61L 2209/22* (2013.01)

(58) Field of Classification Search
    CPC ............. A61L 2209/15; A61L 2209/22; D06F 58/203; A45D 20/122
    See application file for complete search history.

(56) References Cited

U.S. PATENT DOCUMENTS

| | | |
|---|---|---|
| 5,761,824 A | 6/1998 | Moon et al. |
| 9,743,737 B1 | 8/2017 | Malbrough |
| 2007/0137060 A1 | 6/2007 | Woodson |
| 2009/0083986 A1 | 4/2009 | Langley |

FOREIGN PATENT DOCUMENTS

| | | |
|---|---|---|
| JP | 2003-38079 A | 2/2003 |
| JP | 2006283745 A | 10/2006 |

\* cited by examiner

DISPOSABLE CONTAINER

FIELD OF INVENTION

The present invention relates to a disposable container. In particular, the disposable container of the present invention is affixed to an air flow stream of an air flow means which enables an internal air flow (A-A') or an external air flow (B-B') through an opening passage with a closed empty space therebetween the container. The disposable container (100) is use particularly for vaporization, evaporation or diffusion whereby filler materials of filler means are released into the air flow stream through air flow means.

BACKGROUND ART

Currently, diffusers or vaporizers are permanently affixed to a device and specific for use of a single application. There is indeed a need for improved diffusers over diffusers which are currently available.

One example of a hair diffuser is disclosed in U.S. Pat. No. 9,743,737 B1 (hereinafter referred to as US '737 B1 Patent) entitled "Universal Hair Scent Diffuser" having a filing date of 20 Jul. 2015 (Applicant: Malbrough). The US '737 B1 Patent relates to a scented universal hair diffuser. More specifically, the invention pertains to an apparatus which can be removably attached to a conventional hair diffuser head and houses an aroma disc or sheet therein that disperses a selected scent when attached to and acted upon by a hot air stream from a conventional hand held hair dryer. The US '737 B1 Patent provides a simple and efficient means for attaching a universal hair scent diffuser to a conventional hand held hair dryer, i.e., hand blow dryer, the diffuser also housing an aromatic or scented disc or sheet that can be easily replaced or removed as necessary. The preferred embodiment of the universal hair scent diffuser comprises a hollow upper body having an open end housing an interior lining therein made of rubber or other appropriate heat resistant elastomeric material, wherein the lining is graduated in structure at the open end to facilitate a press fit or similar type connection to a barrel end of a conventional hand hair dryer.

Another example is disclosed in United States Patent Application Publication No. US 2009/0083986 A1 (hereinafter referred to as US '986 A1 Publication) entitled "Conditioner Infuser for Hair Dryer Attachment" having a filing date of 27 Sep. 2007 (Applicant: Langley et al.). The US '986 A1 Publication discloses a conditioner infuser cartridge for use with a dryer attachment having an attachment end for engagement with a hair dryer barrel, an opposite air outlet end and a perforated portion between the ends having at least one air intake, the cartridge configured for engagement near the attachment end and including a conditioner element constructed and arranged for retaining a supply of vaporizable conditioner and a support frame receiving the conditioner element and securing same in the attachment.

A further example is disclosed in Japanese Patent No. JPH09201407 (hereinafter referred to as the JP '407 Patent) entitled "Apparatus for Vaporizing and Diffusing Liquid" (Applicant: Suzuki Masakazu). The JP '407 Patent relates to an apparatus for vaporizing and diffusing a liquid into the atmosphere, and more particularly to an apparatus for vaporizing and diffusing a liquid into the atmosphere, such as an air freshener, a deodorant, a sterilizing agent, a repellent for preventing a specific type of animal from approaching.

The advantage of having a disposable container for universal application as described in the present application provides for a single use as compared to conventional types which is permanently affixed to a device and specific for use of a single application.

SUMMARY OF INVENTION

The present invention relates to a disposable container. In particular, the disposable container of the present invention is affixed to an air flow stream of an air flow means which enables an internal air flow (A-A') or an external air flow (B-B') through an opening passage with a closed empty space therebetween the container. The disposable container (100) is use particularly for vaporization, evaporation or diffusion whereby filler materials of filler means are released into the air flow stream through air flow means.

One aspect of the invention provides a disposable container (100) having an opening passage with a closed empty space therebetween. The disposable container (100) comprising filler means (101) filled with filler materials within the closed empty space between an inner side wall (101a) and an outer side wall (101b) and a top (101c) and a bottom part (101d) of the disposable container (100); and locking means (104) at the bottom part of the disposable container (100) to further secure the disposable container (100) to an air flow means. The inner side wall (101a), the outer side wall (101b), the top (101c) and the bottom part (101d) of the disposable container (100) are permeable or perforated enabling filler materials to be released into an air flow stream through air flow means; wherein filler materials are released by means of vaporization, evaporation or diffusion.

Preferably, the bottom part (101d) of the disposable container (100) having a magnetic surface.

Another aspect of the invention provides that the air flow means includes a hair dryer (500) having means for moisturizing, treating and scenting of hair; a cloth dryer (600) having means for scenting and steaming of fabric; and an air blower having means for freshening and fragrancing.

A further aspect of the invention provides that the filler materials are filled into the filler means through injection as gel form, filled as pre-configured solid form, filled as liquid form or filled as powder form.

Yet another aspect of the invention provides that the disposable container (100) is a universal container.

Still another aspect of the invention provides that the air flow stream includes both heated and non-heated air flow.

A further aspect of the invention provides that the air flow stream is of an air flow direction which is parallel to the outer and inner side walls of disposable container.

Yet another aspect of the invention provides that the locking means (104) provides for locking of the disposable container to an accessory fixator to secure the disposable container (100) to an air flow means.

Still another aspect of the invention provides that the disposable container (100) includes a container molded by an absorbent or an adsorbent material having filler materials absorbed within the container.

The present invention consist of features and a combination of parts hereinafter fully described and illustrated in the accompanying drawings, it being understood that various changes in the details may be made without departing from the scope of the invention or sacrificing any of the advantages of the present invention.

BRIEF DESCRIPTION OF ACCOMPANYING DRAWINGS

To further clarify various aspects of some embodiments of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the accompanying drawings.

FIG. 1.0 illustrates a disposable container of the present invention.

FIG. 1.0a illustrates a top view of the disposable container of the present invention.

FIG. 1.0b illustrates a cross-sectional view of the disposable container of the present invention.

FIG. 2.0 illustrates a sectional view of the disposable container of the present invention.

FIG. 3.0 illustrates a bottom view of the disposable container of the present invention.

FIG. 4.0 illustrates an accessory fixator which is secured to the disposable container.

FIG. 5.0 illustrates an example of the disposable container affixed to a hair dryer.

FIG. 6.0 illustrates an example of the disposable container affixed to a drum of clothes dryer.

DETAILED DESCRIPTION OF THE PREFERRED EMBODIMENTS

The present invention relates to a disposable container. In particular, the disposable container of the present invention is affixed to an air flow stream of an air flow means which enables an internal air flow (A-A') or an external air flow (B-B') through an opening passage with a closed empty space therebeween the container. The disposable container (100) is use particularly for vaporization, evaporation or diffusion whereby filler materials of filler means are released into the air flow stream through air flow means. Hereinafter, this specification will describe the present invention according to the preferred embodiments. It is to be understood that limiting the description to the preferred embodiments of the invention is merely to facilitate discussion of the present invention and it is envisioned without departing from the scope of the appended claims.

Figure 1:
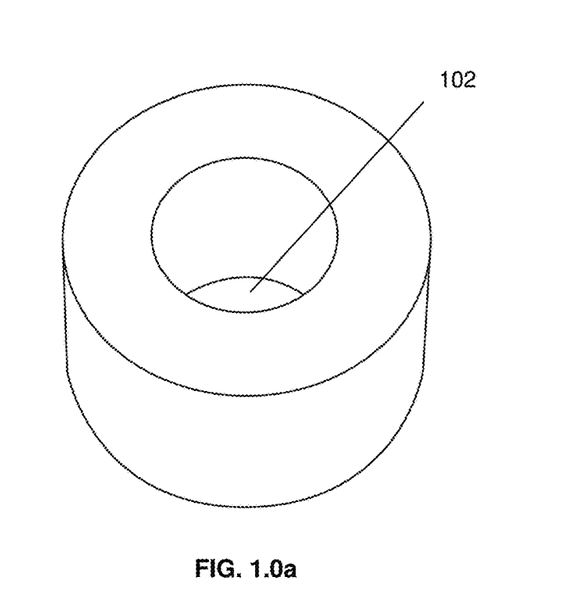
Figure 10:
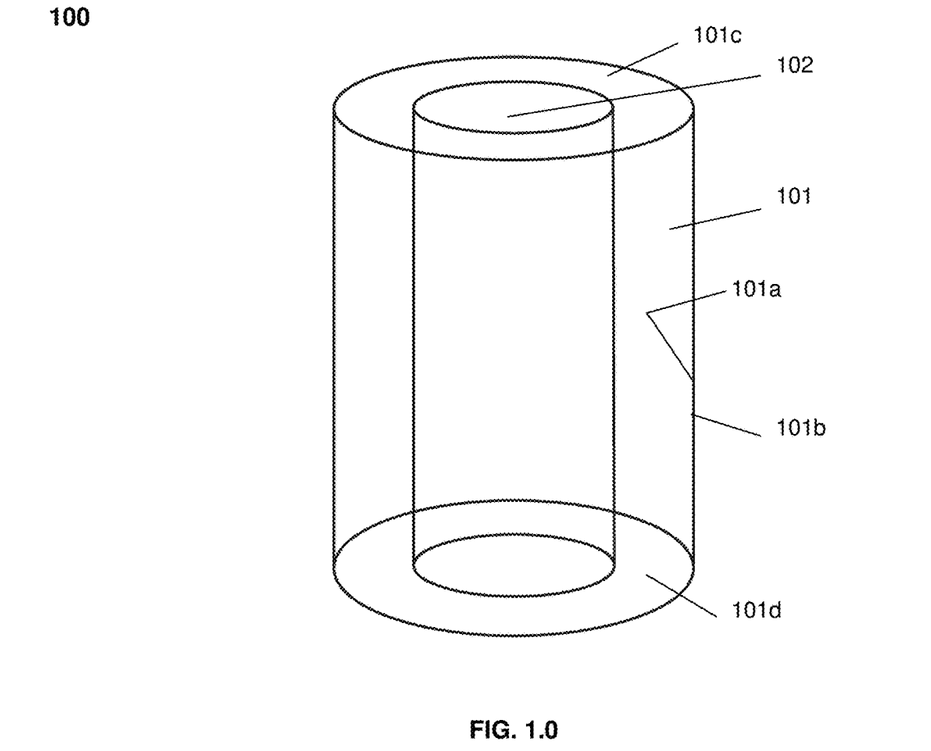

Reference is made to FIG. 1.0 and FIG. 1.0a. FIG. 1.0 illustrates a disposable container while FIG. 1.0a illustrates a top view of the disposable container of the present invention. The disposable container (100) having an opening passage with a closed empty space therebetween further comprising filler means (101) filled with filler materials within the closed empty space between an inner side wall (101a) and an outer side wall (101b) and a top (101c) and a bottom part (101d) of the disposable container (100); and locking means (104) at the bottom part of the disposable container (100) to further secure the disposable container (100) to an air flow means. The inner side wall (101a), the outer side wall (101b), the top (101c) and the bottom part (101d) of the disposable container (100) are permeable or perforated enabling filler materials to be released into an air flow stream through air flow means; wherein filler materials are released by means of vaporization, evaporation or diffusion. The filler materials are filled into the filler means (101) through injection as gel form, filled as pre-configured solid form, filled as liquid form or filled as powder form. The filler means (101) may have more than one form at one time, for example, gel and solid form or gel and powder form.

Figure 20:
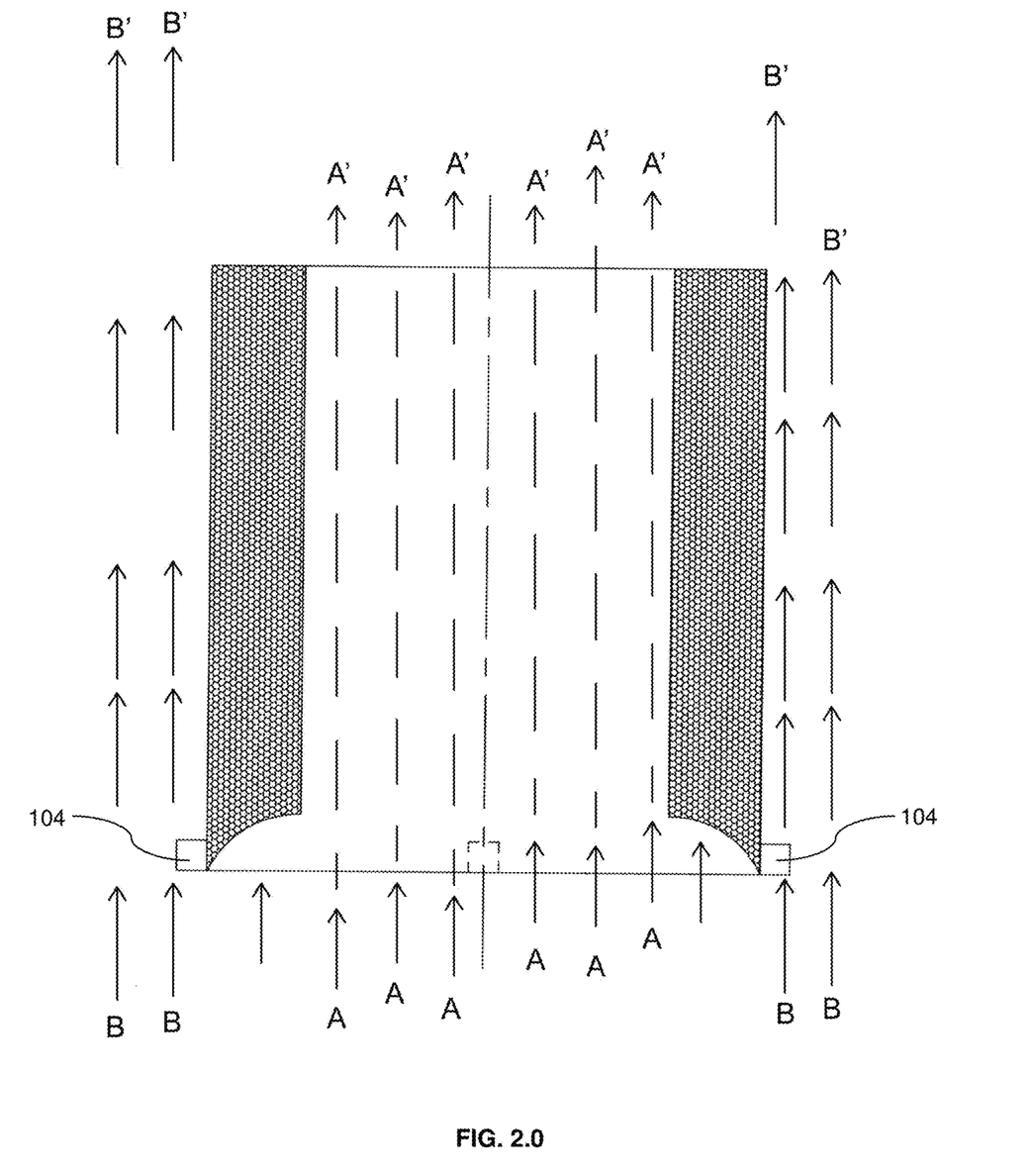
Figure 30:
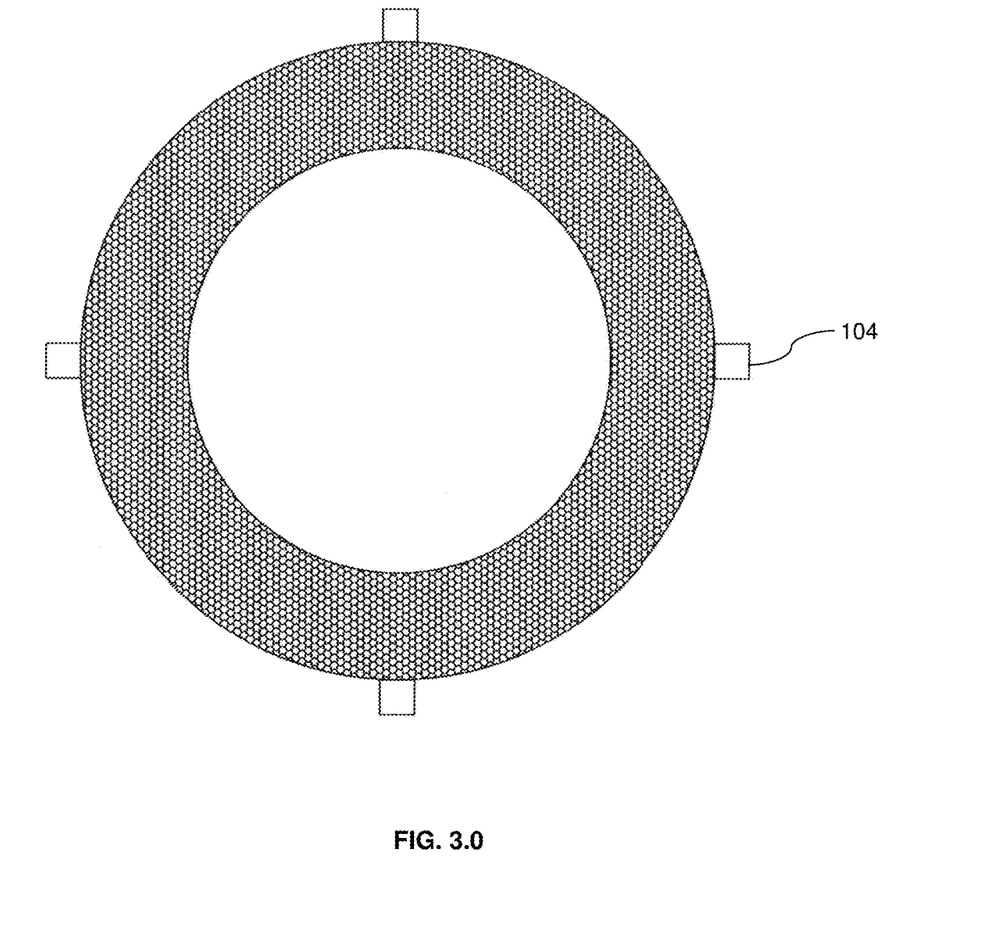

Reference is now made to FIG. 1.0b, FIG. 2.0 and FIG. 3.0. FIG. 1.0b illustrates a cross-sectional view of the disposable container of the present invention while FIG. 2.0 illustrates a sectional view of the disposable container of the present invention and FIG. 3.0 illustrates a bottom view of the disposable container of the present invention. As illustrated in FIG. 1.0b and FIG. 2.0, the opening passage with a closed empty space therebetween (102) enables an internal air flow (A-A') from a bottom of the container to the top portion of the container. Preferably, the bottom part (101d) of the disposable container is of a magnetic surface. The disposable container (100) is secured to a heated or non heated air flow stream of the air flow means whereby the air flow passes through or over or within the container (100) whereby the air flow stream is of an air flow direction which is parallel to the outer and inner side walls of the disposable container (100).

Figure 40:
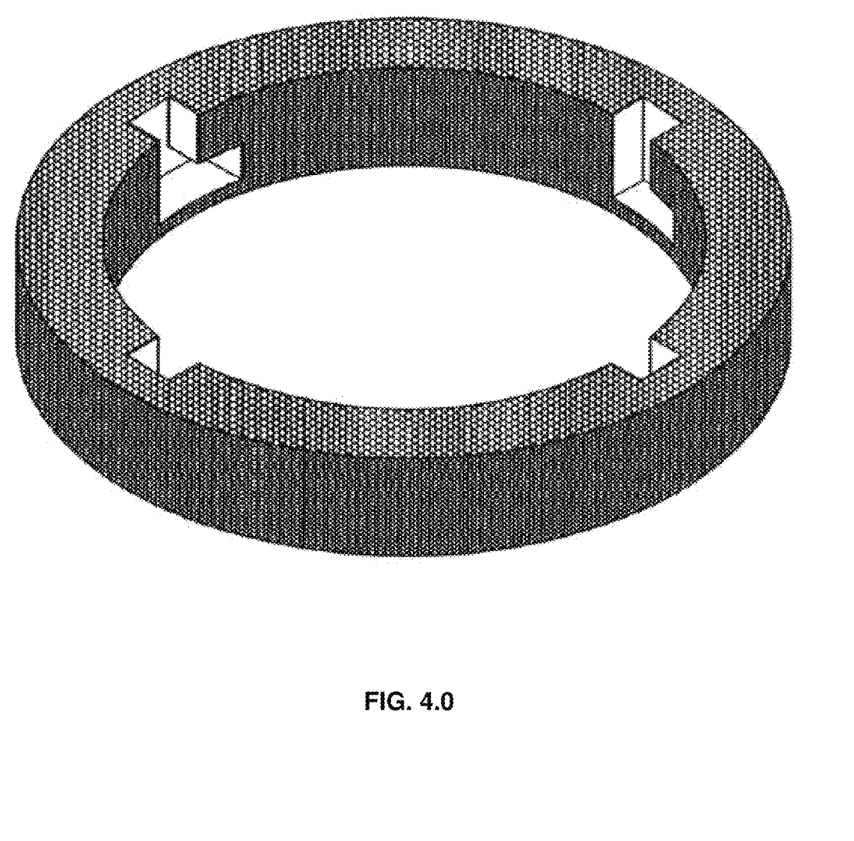

Reference is now made to FIG. 4.0 which illustrates an accessory fixator which is secured to the disposable container. The locking means (104) of the disposable container (100) provides for locking of the disposable container to an accessory fixator to secure the disposable container (100) to an air flow means. The locking means (104) affixed at edges of the container (100) secures the container to an air flow means through a press fit connection or a snap fit connection. The fixative notch (104) is a form of locking means which can be replaced with any form of locking means that secures the container (100) to an air flow means. The application of the locking means such as the fixative notch (104) in a hair dryer is a means to secure the container (100) on the desired application. For example, in a hair dryer, it will be used with an accessory such as a nozzle concentrator whereby the locking means may have tiny holes enabling thin threads or strings on the locking means to be inserted on the hair dryer nozzle. Alternatively, if the container (100) is to be used on a clothes dryer, the locking means such as a fixative notch (104) can be inserted on the inlet air to the drying drum. The container can be of any material not limiting to metallic, stainless steel of plastic.

Figure 50:
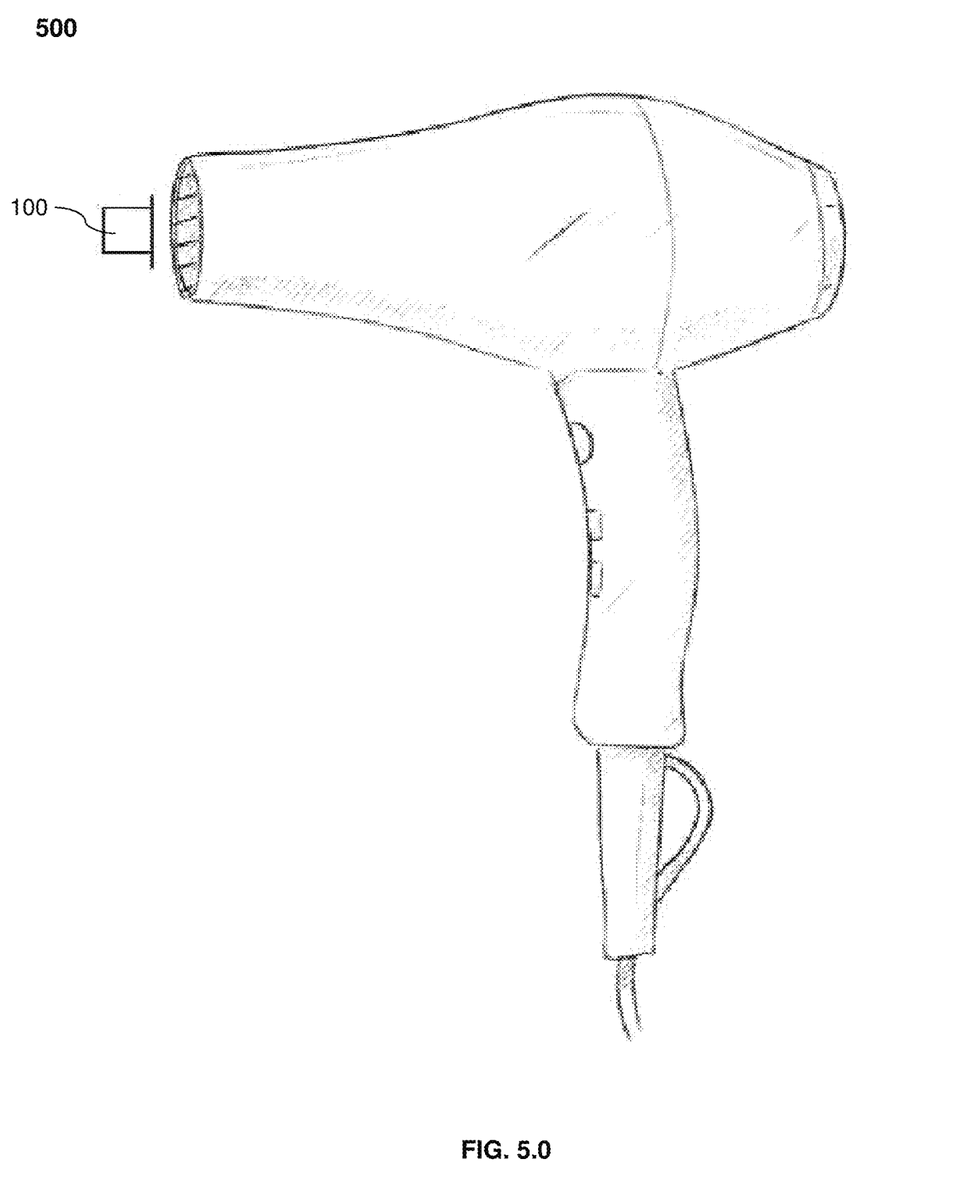
Figure 60:
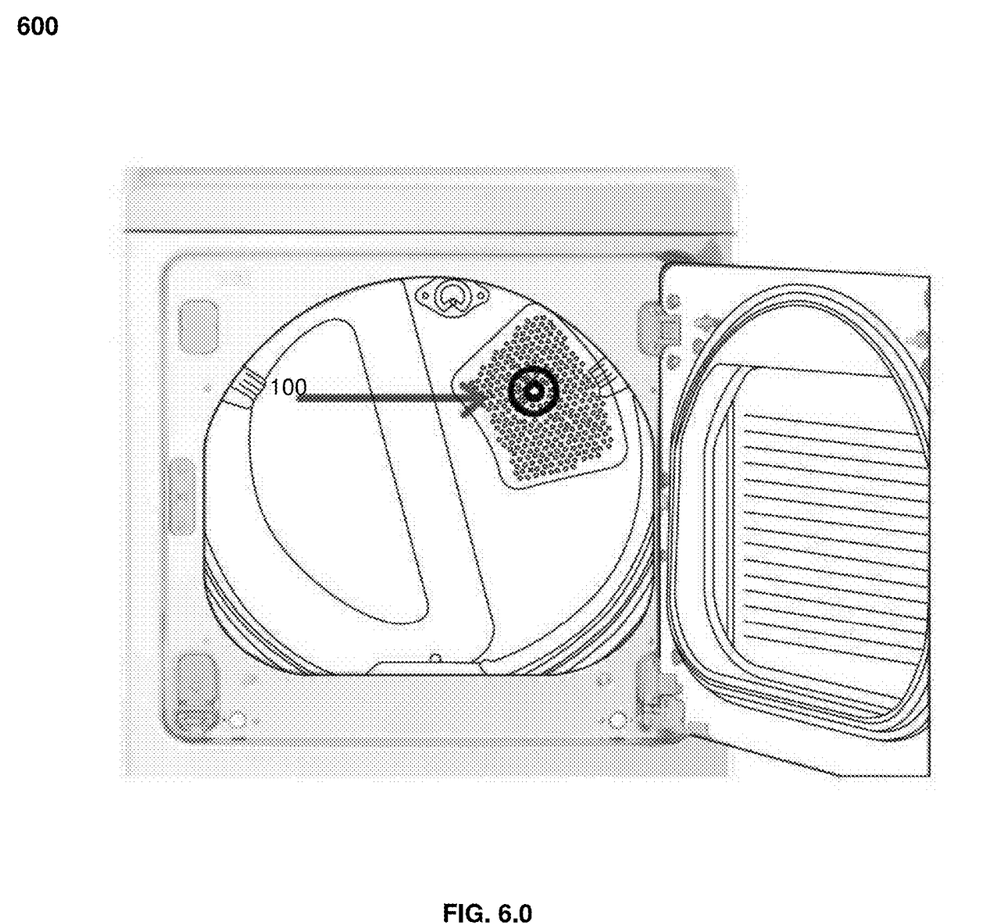

The disposable container (100) is a universal container which is an accessory to various applications of air flow means which includes a hair dryer, clothes dryer and an air blower but not limited to the same. Reference is now made to FIG. 5.0 and FIG. 6.0 respectively. FIG. 5.0 illustrates an example of the disposable container affixed to a hair dryer while FIG. 6.0 illustrates an example of the disposable container affixed to a drum of clothes dryer. For application of the disposable container (100) to a hair dryer, the disposable container (100) is affixed to a nozzle of the hair dryer, hair dryer comb attachment, hair dryer brush attachment, hair dryer attachment or any other available fixtures to the hair dryer. For application of the disposable container (100) to a clothes dryer, the disposable container (100) is affixed to an air flow outlet of a drum of the clothes dryer enabling vaporization or diffusion or evaporation of the fragrance from the container (100). The air flow means includes a hair dryer (500) having means for moisturizing, treating and scenting of hair; a cloth dryer (600) having means for scenting and steaming of fabric; and an air blower having means for freshening and fragrancing. Treatment means includes moisture infusion of the contents of the filler materials into the specific application. For example, moisture infusion of the contents of the filler materials is infused into hair from the container which is affixed to a hair dryer.

In another embodiment, the disposable container (100) includes a container molded by an absorbent or an adsorbent material having filler materials absorbed within the container.

The advantage of having a disposable container (100) for universal application provides for a single use as compared to conventional type which is permanently affixed to a device and specific for use of a single application.

Unless the context requires otherwise or specifically stated to the contrary, integers, steps or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of steps, elements or integers. Thus, in the context of this specification, the term "comprising" is used in an inclusive sense and thus should be understood as meaning "including principally, but not necessarily solely".

The invention claimed is:

1. A disposable container, further comprising:
    filler means filled with filler materials within an empty space of the disposable container, between an inner side wall, an outer side wall, a top part, and a bottom part of the disposable container;
    an opening passage through the filler means defined by the inner side wall, extending from the top part to the bottom part of the disposable container; and
    locking means at the bottom part of the disposable container to further secure the disposable container to an air flow source;
    wherein:
        the inner side wall, the outer side wall, the top part, and the bottom part of the disposable container are permeable or perforated, enabling the filler materials to be released into an air flow stream through air flow means;
        the air flow stream is of an air flow direction through the opening passage which is parallel to the outer side wall and the inner side wall of the disposable container; and
        the filler materials are released by means of vaporization, evaporation or diffusion.

2. The disposable container according to claim 1, wherein the bottom part of the disposable container includes a magnetic surface.

3. The disposable container according to claim 1, wherein the air flow means includes a hair dryer having means for moisturizing, treating and scenting of hair; a cloth dryer having means for scenting and steaming of fabric; and an air blower having means for freshening and fragrancing.

4. The disposable container according to claim 1, wherein the filler materials are filled into the filler means through injection as gel form, filled as pre-configured solid form, filled as liquid form or filled as powder form.

5. The disposable container according to claim 1, wherein the disposable container is a universal container.

6. The disposable container according to claim 1, wherein the air flow stream includes both heated and non-heated air flow.

7. The disposable container according to claim 1, wherein the locking means provides for locking of the disposable container to an accessory fixator to secure the disposable container to an air flow means.

8. The disposable container according to claim 1, wherein the disposable container includes a container molded by an absorbent or an adsorbent material having filler materials absorbed within the container.

* * * * *